United States Patent
Sing et al.

(10) Patent No.: US 9,084,787 B2
(45) Date of Patent: **\*Jul. 21, 2015**

(54) METHODS OF TREATING SPINAL CORD INJURY AND MINIMIZING SCARRING

(71) Applicant: Stemnion, Inc., Pittsburgh, PA (US)

(72) Inventors: George L Sing, New York, NY (US); Diana L Clarke, Pittsburgh, PA (US); Vivienne S Marshall, San Antonio, TX (US)

(73) Assignee: STEMNION, INC., Pittsburgh, PA (US)

( * ) Notice: Subject to any disclaimer, the term of this patent is extended or adjusted under 35 U.S.C. 154(b) by 156 days.

This patent is subject to a terminal disclaimer.

(21) Appl. No.: 13/793,593

(22) Filed: Mar. 11, 2013

(65) Prior Publication Data

US 2013/0189235 A1    Jul. 25, 2013

Related U.S. Application Data

(60) Division of application No. 11/986,961, filed on Nov. 27, 2007, now Pat. No. 8,475,788, which is a continuation-in-part of application No. PCT/US2007/013140, filed on Jun. 4, 2007.

(60) Provisional application No. 60/813,759, filed on Jun. 14, 2006.

(51) Int. Cl.
| | |
|---|---|
| *A61K 35/50* | (2015.01) |
| *C12N 5/0735* | (2010.01) |
| *A61K 35/12* | (2015.01) |
| *A61K 35/48* | (2015.01) |
| *C12N 5/073* | (2010.01) |
| *A61K 45/06* | (2006.01) |

(52) U.S. Cl.
CPC ............... *A61K 35/50* (2013.01); *A61K 35/48* (2013.01); *A61K 45/06* (2013.01); *C12N 5/0605* (2013.01); *A61K 35/12* (2013.01)

(58) Field of Classification Search
CPC ....... A61K 35/12; A61K 35/48; A61K 35/50; A61K 45/06; C12N 5/0605

USPC ........................................................ 424/93.7
See application file for complete search history.

(56) References Cited

U.S. PATENT DOCUMENTS

| | | |
|---|---|---|
| 2004/0161419 A1 | 8/2004 | Strom et al. |
| 2005/0032209 A1 | 2/2005 | Messina et al. |
| 2005/0152995 A1 | 7/2005 | Chen et al. |
| 2006/0030039 A1 | 2/2006 | Chen et al. |
| 2006/0233765 A1 | 10/2006 | Messina et al. |
| 2006/0233766 A1 | 10/2006 | Messina et al. |

OTHER PUBLICATIONS

Spinal Cord Injury. Health & Disease information. dated Oct. 31, 2006. downloaded from www.hmc.psu.edu/healthinfo/s/spinalcordinjury.htm on.p. 1-3.*
Spinal cord injury cure. downloaded from www.fscip.org/cure.htm on May 17, 2010. p. 1-3.*
Anderson, A.J., et al., J Neurotrauma 2004 21(12):1831-46.
Pallini, R., et al., Neurosurgery 2005 57(5):1014-25.
Cummings, B.J., et al., PNAS 2005 102(39):14069-14074.
Cummings, B.J., et al., Neural Res 2006 28(5):474-81.
Sankar, V., et al., Neuroscience 2003 118:11-17.
Wu, Z-Y., et al., Chinese Medical Journal 2006 119(24):2101-2107.
Parolina, O., et al., Stem Cells 2008 26:300-311.
Uchida, S., et al. J Neuroscience 2000 62:585-590.

* cited by examiner

*Primary Examiner* — Taeyoon Kim
(74) *Attorney, Agent, or Firm* — Linda O. Palladino; Gail M. Kempler

(57) ABSTRACT

The invention is directed to methods of promoting the healing of spinal cord injury. The invention is further directed to methods of minimizing the extent of scarring following spinal cord injury. Such methods utilize novel compositions, including but not limited to extraembryonic cytokine secreting cells (herein referred to as ECS cells), including, but not limited to, amnion-derived multipotent progenitor cells (herein referred to as AMP cells) and conditioned media derived therefrom (herein referred to as amnion-derived cellular cytokine solution or ACCS), each alone or in combination with each other and/or other agents.

6 Claims, No Drawings

METHODS OF TREATING SPINAL CORD INJURY AND MINIMIZING SCARRING

CROSS-REFERENCE TO RELATED APPLICATION

This application is a divisional application of U.S. application Ser. No. 11/986,961, filed Nov. 27, 2007, now U.S. Pat. No. 8,475,788 and claims priority under 35 USC §119(e) to U.S. Provisional Application No. 60/813,759, filed Jun. 14, 2006, and under 35 USC §119(a) to PCT International Application US07/013140, filed Jun. 4, 2007, the contents of which are incorporated herein by reference in their entirety.

FIELD OF THE INVENTION

The field of the invention is directed to methods of promoting the healing of spinal cord injury. The field of the invention is further directed to methods of minimizing the extent of scarring following spinal cord injury. Such methods utilize novel compositions, including but not limited to extraembryonic cytokine secreting cells (herein referred to as ECS cells), including, but not limited to, amnion-derived multipotent progenitor cells (herein referred to as AMP cells) and conditioned media derived therefrom (herein referred to as amnion-derived cellular cytokine solution or ACCS), each alone or in combination with each other and/or other agents.

DESCRIPTION OF RELATED ART

Cummings, B. J., et al. (Neurol Res 2006 28(5):474-81) studied human neural stem cell differentiation following transplantation into spinal cord injured NOD SCID mice and reported that human fetal CNS-derived stem cells grown as neurospheres survive, migrate and express differentiation markers for neurons and oligodendrocytes.

Cummings, B. J., et al., (PNAS USA 2005 102(39):14069-74) report that human CNS stem cells grown as neurospheres survive, migrate and express differentiation markers for neurons and oligodendrocytes after long-term engraftment in spinal cord-injured NOD SCID mice.

Pallini, R., et al., (Neurosurgery 2005 57(5):1014-25) studied homologous transplantation of murine neural stem cells to the injured spinal cord of mice and reported that neural stem cells grafting improved motor recovery.

Sankar, V. et al., (Neuroscience 2003, Letter to Neuroscience, 118(1):11-7) studied the role of human amniotic epithelial cell transplantation in transected spinal cord injury repair and reported that the human amniotic epithelial cells survived in monkey transected spinal cord, the graft was penetrated by host axons and there was no glial scar at the transection lesion site.

Wu, Z-Y., et al, (Chinese Med Jour 2006, 119(24):2101-07) reported that transplantation of human amniotic epithelial cells improves hindlimb function in rats with spinal cord injury.

BACKGROUND OF THE INVENTION

Spinal cord injury occurs when axons or nerve fibers of the spinal cord are interrupted, generally by mechanical forces. If the spinal cord is compressed, severed or contused, the axons may be physically or physiologically disintegrated, so that no conduction of neuroelectric impulses can occur along the affected axon's length. Eventually, large populations of axons and their associated cell bodies may die, causing massive loss in communication between the brain and the peripheral nerves, resulting in varying degrees of functional deficit. Currently available therapies have demonstrated only limited success in restoring function following spinal cord injury.

The fibrous scar that develops after spinal cord injury is considered a major impediment for axonal regeneration. Spinal cord scarring generally means the recruitment and proliferation of glial cells to the site of injury. The densely packed cells (primarily reactive astrocytes) and their secretions form a dense cellular plaque known as the glial scar. This scar prevents axons from projecting through. In response to injury to the central nervous system (CNS), reactive astrocytes appear and accumulate in the wounded area, leading to glial scar formation. Glial scar is the physical barrier to axonal regeneration of injured neurons. Chondroitin sulfate proteoglycans are inhibitory to axon outgrowth and are upregulated in reactive astrocytes upon CNS injury. It is known that keratin sulfate proteoglycans (KSPGs) are also augmented after CNS injury and act as inhibitory cues.

Therapeutic treatments aimed at suppression of fibrous scarring have been shown to promote axon regeneration in various lesion paradigms of the mammalian spinal cord.

To date, no treatment option exists that is able to promote healing, reduce fibrous scarring, ameliorate cellular damage following spinal cord injury, provide neuroprotection or induce the growth and development of spinal cord cells to replace damaged or dead cells, any or all of which could help return the injured patient to normal or near normal function. Therefore, it is an object of the instant invention to provide such treatment options for spinal cord injury patients.

BRIEF SUMMARY OF THE INVENTION

The development of a cell-based therapy that could be administered concomitant with spinal cord injury stabilization surgery early after injury would be clinically useful. In addition, a cell-based therapy that could minimize secondary damage and/or promote wound healing following spinal cord injury could optionally be combined with a variety of regenerative strategies currently in clinical trial (e.g. IN-1 anti-NOGO, rollipram, etc.) to promote functional recovery in the injured individual. It is generally agreed in the spinal cord injury field that such combinatorial approaches may be key to succeeding in significantly affecting recovery of function in the human clinical setting.

Accordingly, it is an object of the instant invention to provide such methods for promoting healing following spinal cord injury by administering extraembryonic cytokine secreting cells (herein referred to as ECS cells), including, but not limited to, amnion-derived multipotent progenitor cells (herein referred to as AMP cells) and conditioned media derived therefrom (herein referred to as amnion-derived cellular cytokine solution or ACCS), each alone or in combination with each other and/or other agents and/or other treatment modalities such as therapeutic cooling, thus improving healing and functional recovery. It is also an object of the instant invention to minimize the extent of scarring following spinal cord injury by administering extraembryonic cytokine secreting cells (herein referred to as ECS cells), including, but not limited to, amnion-derived multipotent progenitor cells (herein referred to as AMP cells) and conditioned media derived therefrom (herein referred to as amnion-derived cellular cytokine solution or ACCS), each alone or in combination with each other and/or other agents and/or treatment modalities such as therapeutic cooling, thus improving healing and functional recovery.

Accordingly, a first aspect of the invention is a method for treating spinal cord injury in a patient in need thereof comprising administering to the patient a therapeutically effective amount of one or more compositions comprising ECS cells, conditioned media derived therefrom, cell lysate derived therefrom or cell products derived therefrom. In one embodiment the ECS cells are AMP cells. In another embodiment the conditioned media is ACCS. In a particular embodiment the AMP cells are pooled AMP cells and in another particular embodiment, the ACCS is pooled ACCS. In another particular embodiment, the AMP cells and ACCS, either pooled or non-pooled, are used in combination.

A second aspect of the invention is method for promoting the healing of a spinal cord injury in a patient in need thereof comprising administering to the patient a therapeutically effective amount of one or more compositions comprising ECS cells, conditioned media derived therefrom, cell lysate derived therefrom or cell products derived therefrom. In one embodiment the ECS cells are AMP cells. In another embodiment the conditioned media is ACCS. In a particular embodiment the AMP cells are pooled AMP cells and in another particular embodiment, the ACCS is pooled ACCS. In another particular embodiment, the AMP cells and ACCS, either pooled or non-pooled, are used in combination.

A third aspect of the invention is a method for stimulating growth or regeneration of spinal cord cells following spinal cord injury in a patient in need thereof comprising administering to the patient a therapeutically effective amount of one or more compositions comprising ECS cells, conditioned media derived therefrom, cell lysate derived therefrom or cell products derived therefrom. In one embodiment the ECS cells are AMP cells. In another embodiment the conditioned media is ACCS. In a particular embodiment the AMP cells are pooled AMP cells and in another particular embodiment, the ACCS is pooled ACCS. In another particular embodiment, the AMP cells and ACCS, either pooled or non-pooled, are used in combination. In still another embodiment the spinal cord cells are neurons, oligodendrocytes, astrocytes, microglial cells, ependymal cells, or Schwann cells. In another particular embodiment the neurons are motor neurons, interneurons or sensory neurons.

A fourth aspect of the invention is a method for preventing or ameliorating scarring following spinal cord injury in a patient in need thereof comprising administering to the patient a therapeutically effective amount of one or more compositions comprising ECS cells, conditioned media derived therefrom, cell lysate derived therefrom or cell products derived therefrom. In one embodiment the ECS cells are AMP cells. In another embodiment the conditioned media is ACCS. In a particular embodiment the AMP cells are pooled AMP cells and in another particular embodiment, the ACCS is pooled ACCS. In another particular embodiment, the AMP cells and ACCS, either pooled or non-pooled, are used in combination.

A fifth aspect of the invention is a method for neuroprotecting spinal cord neurons following spinal cord injury in a patient in need thereof comprising administering to the patient a therapeutically effective amount of one or more compositions comprising ECS cells, conditioned media derived therefrom, cell lysate derived therefrom or cell products derived therefrom. In one embodiment the ECS cells are AMP cells. In another embodiment the conditioned media is ACCS. In a particular embodiment the AMP cells are pooled AMP cells and in another particular embodiment, the ACCS is pooled ACCS. In another particular embodiment, the AMP cells and ACCS, either pooled or non-pooled, are used in combination.

In particular embodiments of aspects one, two, three, four and five of the invention the spinal cord injury is complete spinal cord injury or incomplete spinal cord injury. In even more particular embodiments, the spinal cord injury is caused by contusion of the spinal cord, bruising of the spinal cord, loss of blood to the spinal cord, pressure on the spinal cord, cut spinal cord or severed spinal cord and the incomplete spinal cord injury is anterior cord syndrome, central cord syndrome, Brown-Sequard syndrome, injuries to individual nerve cells or spinal contusion.

In a preferred embodiment of all aspects of the invention, the patient is a human.

In particular embodiments of aspects one, two, three, four and five of the invention, the ECS cells, conditioned media derived therefrom, cell lysate derived therefrom or cell products derived therefrom are administered in combination with other agents. In specific embodiment, the other agents are active agents. In particular specific embodiments the active agents are neuroregenerative agents, neuroprotective agents, neurotrophic factors, growth factors, cytokines, chemokines, antibodies, inhibitors, antibiotics, immunosuppressive agents, steroids, anti-fungals, anti-virals or other cell types. In even more particular embodiments, the neuroprotective agent is for example dopamine D3 receptor agonists, the neurotrophic factors are for example BDNF, NT-3, NT-4, CNTF, NGF, or GDNF; the antibodies are for example IN-1 anti-NOGO antibodies; the inhibitor is for example the PDE4 inhibitor rollipram; the immunosuppressive agents are for example corticosteroids (i.e. glucocorticoids), cyclosporine, tacrolimus, sirolimus, methotrexate, azathiopine, mercatopurine, cytotoxic antibiotics, polyclonal and monoclonal antibodies such as anti-T-cell receptor (CD23) and anti-IL2 receptor (CD25) antibodies, interferon, opioids, TNF binding proteins, mycophenolate, and small biological agents such as FTY720; the antibiotics are pikromycin, narbomycin, methymycin, neomethymycin; the steroid is methylprednisolone; and the other cell types are for example differentiated AMP cells, or a mixture of differentiated and undifferentiated AMP cells, or a mixture of AMP cells (differentiated and/or undifferentiated) and other cells such as neural stem cells or any other progenitor cell or cells that are treated in such a way as to augment the AMP cells or AMP cell activity.

In particular embodiments of aspects one, two, three, four and five of the invention, the ECS cells, conditioned media derived therefrom, cell lysate derived therefrom or cell products derived therefrom are administered in combination with other treatment modalities such as, for example, therapeutic cooling.

DEFINITIONS

As defined herein "isolated" refers to material removed from its original environment and is thus altered "by the hand of man" from its natural state.

As defined herein, a "gene" is the segment of DNA involved in producing a polypeptide chain; it includes regions preceding and following the coding region, as well as intervening sequences (introns) between individual coding segments (exons).

As used herein, the term "protein marker" means any protein molecule characteristic of the plasma membrane of a cell or in some cases of a specific cell type.

As used herein, "enriched" means to selectively concentrate or to increase the amount of one or more materials by elimination of the unwanted materials or selection and separation of desirable materials from a mixture (i.e. separate cells with specific cell markers from a heterogeneous cell population in which not all cells in the population express the marker).

As used herein, the term "substantially purified" means a population of cells substantially homogeneous for a particular marker or combination of markers. By substantially homogeneous is meant at least 90%, and preferably 95% homogeneous for a particular marker or combination of markers.

The term "placenta" as used herein means both preterm and term placenta.

As used herein, the term "totipotent cells" shall have the following meaning. In mammals, totipotent cells have the potential to become any cell type in the adult body; any cell type(s) of the extraembryonic membranes (e.g., placenta). Totipotent cells are the fertilized egg and approximately the first 4 cells produced by its cleavage.

As used herein, the term "pluripotent stem cells" shall have the following meaning. Pluripotent stem cells are true stem cells with the potential to make any differentiated cell in the body, but cannot contribute to making the components of the extraembryonic membranes which are derived from the trophoblast. The amnion develops from the epiblast, not the trophoblast. Three types of pluripotent stem cells have been confirmed to date: Embryonic Stem (ES) Cells (may also be totipotent in primates), Embryonic Germ (EG) Cells, and Embryonic Carcinoma (EC) Cells. These EC cells can be isolated from teratocarcinomas, a tumor that occasionally occurs in the gonad of a fetus. Unlike the other two, they are usually aneuploid.

As used herein, the term "multipotent stem cells" are true stem cells but can only differentiate into a limited number of types. For example, the bone marrow contains multipotent stem cells that give rise to all the cells of the blood but may not be able to differentiate into other cells types.

As used herein, the term "extraembryonic tissue" means tissue located outside the embryonic body which is involved with the embryo's protection, nutrition, waste removal, etc. Extraembryonic tissue is discarded at birth. Extraembryonic tissue includes but is not limited to the amnion, chorion (trophoblast and extraembryonic mesoderm including umbilical cord and vessels), yolk sac, allantois and amniotic fluid (including all components contained therein). Extraembryonic tissue and cells derived therefrom have the same genotype as the developing embryo.

As used herein, the term "extraembryonic cytokine secreting cells" or "ECS cells" means a population of cells derived from the extraembryonic tissue which have the characteristic of secreting a unique combination of physiologically relevant cytokines in a physiologically relevant temporal manner into the extracellular space or into surrounding culture media. In one embodiment, the ECS cells secrete at least one cytokine selected from VEGF, Angiogenin, PDGF and TGFβ2 and at least one MMP inhibitor selected from TIMP-1 and TIMP-2. In another embodiment, the ECS cells secrete more than one cytokine selected from VEGF, Angiogenin, PDGF and TGFβ2 and more than one MMP inhibitor selected from TIMP-1 and TIMP-2. In a preferred embodiment, the ECS cells secrete the cytokines VEGF, Angiogenin, PDGF and TGFβ2 and the MMP inhibitors TIMP-1 and TIMP-2. The physiological range of the cytokine or cytokines in the unique combination is as follows: ~5-16 ng/ml for VEGF, ~3.5-4.5 ng/ml for Angiogenin, ~100-165 μg/ml for PDGF, ~2.5-2.7 ng/ml for TGFβ2, ~0.68 μg ml for TIMP-1 and ~1.04 μg/ml for TIMP-2. ECS cells may be selected from populations of cells and compositions described in this application and in US2003/0235563, US2004/0161419, US2005/0124003, U.S. Provisional Application Nos. 60/666,949, 60/699,257, 60/742,067, 60/813,759, U.S. application Ser. No. 11/333, 849, U.S. application Ser. No. 11/392,892, PCT U.S. Ser. No. 06/011,392, US2006/0078993, PCT/US00/40052, U.S. Pat. No. 7,045,148, US2004/0048372, and US2003/0032179, the contents of which are incorporated herein by reference in their entirety.

As used herein, the term "amnion-derived multipotent progenitor cell" or "AMP cell" means a specific population of ECS cells that are epithelial cells derived from the amnion. In addition to the characteristics described above for ECS cells, AMP cells have the following characteristics. They grow without feeder layers, do not express the protein telomerase and are non-tumorigenic. AMP cells do not express the hematopoietic stem cell marker CD34 protein. The absence of CD34 positive cells in this population indicates the isolates are not contaminated with hematopoietic stem cells such as umbilical cord blood or embryonic fibroblasts. Virtually 100% of the cells react with antibodies to low molecular weight cytokeratins, confirming their epithelial nature. Freshly isolated AMP cells will not react with antibodies to the stem/progenitor cell markers c-kit (CD117) and Thy-1 (CD90). Several procedures used to obtain cells from full term or pre-term placenta are known in the art (see, for example, US 2004/0110287; Anker et al., 2005, Stem Cells 22:1338-1345; Ramkumar et al., 1995, Am. J. Ob. Gyn. 172: 493-500). However, the methods used herein provide improved compositions and populations of cells. AMP cells have previously been described as "amnion-derived cells" (see U.S. Provisional Application Nos. 60/666,949, 60/699, 257, 60/742,067, U.S. Provisional Application Nos. 60/813, 759, U.S. application Ser. No. 11/333,849, U.S. application Ser. No. 11/392,892, and PCTUS06/011392, each of which is incorporated herein in its entirety).

By the term "animal-free" when referring to certain compositions, growth conditions, culture media, etc. described herein, is meant that no animal-derived materials, such as animal-derived serum, other than human materials, such as native or recombinantly produced human proteins, are used in the preparation, growth, culturing, expansion, or formulation of the certain composition or process.

By the term "expanded", in reference to cell compositions, means that the cell population constitutes a significantly higher concentration of cells than is obtained using previous methods. For example, the level of cells per gram of amniotic tissue in expanded compositions of AMP cells is at least 50 and up to 150 fold higher than the number of cells in the primary culture after 5 passages, as compared to about a 20 fold increase in such cells using previous methods. In another example, the level of cells per gram of amniotic tissue in expanded compositions of AMP cells is at least 30 and up to 100 fold higher than the number of cells in the primary culture after 3 passages. Accordingly, an "expanded" population has at least a 2 fold, and up to a 10 fold, improvement in cell numbers per gram of amniotic tissue over previous methods. The term "expanded" is meant to cover only those situations in which a person has intervened to elevate the number of the cells.

As used herein, the term "passage" means a cell culture technique in which cells growing in culture that have attained confluence or are close to confluence in a tissue culture vessel are removed from the vessel, diluted with fresh culture media (i.e. diluted 1:5) and placed into a new tissue culture vessel to allow for their continued growth and viability. For example, cells isolated from the amnion are referred to as primary cells. Such cells are expanded in culture by being grown in the growth medium described herein. When such primary cells are subcultured, each round of subculturing is referred to as a passage. As used herein, "primary culture" means the freshly isolated cell population.

As used herein, "conditioned medium" is a medium in which a specific cell or population of cells has been cultured, and then removed. When cells are cultured in a medium, they may secrete cellular factors that can provide support to or affect the behavior of other cells. Such factors include, but are not limited to hormones, cytokines, extracellular matrix (ECM), proteins, vesicles, antibodies, chemokines, receptors, inhibitors and granules. The medium containing the cellular factors is the conditioned medium. Examples of methods of preparing conditioned media are described in U.S. Pat. No. 6,372,494 which is incorporated by reference in its entirety herein. As used herein, conditioned medium also refers to components, such as proteins, that are recovered and/or purified from conditioned medium or from ECS cells, including AMP cells.

As used herein, the term "amnion-derived cellular cytokine solution" or "ACCS" means conditioned medium that has been derived from AMP cells or expanded AMP cells, which contains a unique combination of physiologically relevant cytokines at physiologically relevant levels. ACCS has previously been referred to as "amnion-derived cellular cytokine suspension"

The term "physiological level" as used herein means the level that a substance in a living system is found and that is relevant to the proper functioning of a biochemical and/or biological process.

The term "lysate" as used herein refers to the composition obtained when cells, for example, AMP cells, are lysed and optionally the cellular debris (e.g., cellular membranes) is removed. This may be achieved by mechanical means, by freezing and thawing, by sonication, by use of detergents, such as EDTA, or by enzymatic digestion using, for example, hyaluronidase, dispase, proteases, and nucleases.

As used herein, the term "pooled" means a plurality of compositions that have been combined to create a new composition having more constant or consistent characteristics as compared to the non-pooled compositions. For example, pooled AMP cells have more constant or consistent characteristics compared to non-pooled AMP cells and pooled ACCS has more constant or consistent characteristics compared to non-pooled ACCS.

As used herein, the term "substrate" means a defined coating on a surface that cells attach to, grown on, and/or migrate on. As used herein, the term "matrix" means a substance that cells grow in or on that may or may not be defined in its components. The matrix includes both biological and non-biological substances. As used herein, the term "scaffold" means a three-dimensional (3D) structure (substrate and/or matrix) that cells grow in or on. It may be composed of biological components, synthetic components or a combination of both. Further, it may be naturally constructed by cells or artificially constructed. In addition, the scaffold may contain components that have biological activity under appropriate conditions.

The term "cell product" or "cell products" as used herein refers to any and all substances made by and secreted from a cell, including but not limited to, protein factors (i.e. growth factors, differentiation factors, engraftment factors, cytokines, morphogens, proteases (i.e. to promote endogenous cell delamination, protease inhibitors), extracellular matrix components (i.e. fibronectin, etc.).

The term "therapeutically effective amount" means that amount of a therapeutic agent necessary to achieve a desired physiological effect (i.e. promote functional recovery following spinal cord injury).

As used herein, the term "pharmaceutically acceptable" means that the components, in addition to the therapeutic agent, comprising the formulation, are suitable for administration to the patient being treated in accordance with the present invention.

As used herein, the term "therapeutic protein" includes a wide range of biologically active proteins including, but not limited to, growth factors, enzymes, hormones, cytokines, inhibitors of cytokines, blood clotting factors, peptide growth and differentiation factors.

The term "transplantation" as used herein refers to the administration of a composition comprising cells that are either in an undifferentiated, partially differentiated, or fully differentiated form, or a combination thereof, into a human or other animal.

As used herein, the term "differentiation" means the process by which cells become progressively more specialized.

As used herein, the term "differentiation efficiency" means the percentage of cells in a population that are differentiating or are able to differentiate.

As used herein, the term "tissue" refers to an aggregation of similarly specialized cells united in the performance of a particular function.

As used herein, the terms "a" or "an" means one or more; at least one.

As used herein, the term "adjunctive" means jointly, together with, in addition to, in conjunction with, and the like.

As used herein, the term "co-administer" can include simultaneous or sequential administration of two or more agents.

As used herein, the term "central nervous system" or "CNS" means the brain and/or spinal cord.

As used herein, "central nervous system disorder" or "CNS disorder" means any condition or disease that causes or results in a functional and/or physical deficit in the brain and/or spinal cord.

As used herein, the term "neurodegeneration" means the progressive loss of neurons in the central nervous system. This includes but is not limited to immediate loss of neurons followed by subsequent loss of connecting or adjacent neurons.

As used herein, the term "neuroprotection" or "neuroprotecting" means the arrest and/or reverse progression of neurodegeneration following a central nervous system injury.

As used herein, the term "neurological disease" refers to a disease or condition associated with any defects in the entire integrated system of nervous tissue in the body: the cerebral cortex, cerebellum, thalamus, hypothalamus, midbrain, pons, medulla, brainstem, spinal cord, basal ganglia and peripheral nervous system.

"Neuron," "neuronal cell" and "neural cell" (including neural progenitor cells and neural stem cells) are used interchangeably to refer to nerve cells, i.e., cells that are responsible for conducting nerve impulses from one part of the body to another. Most neurons consist of three distinct portions: a cell body which contains the nucleus, and two different types of cytoplasmic processes: dendrites and axons. Dendrites, which are the receiving portion of the neuron, are usually highly branched, thick extensions of the cell body. The axon is typically a single long, thin process that is specialized to conducts nerve impulses away from the cell body to another neuron or muscular or glandular tissue. Axons may have side branches called "axon collaterals." Axon collaterals and axons may terminate by branching into many fine filaments called telodendria. The distal ends of telodendria are called synaptic end bulbs or axonal terminals, which contain synaptic vesicles that store neurotransmitters. Axons may be surrounded by a multilayered, white, phospholipid, segmented covering called the myelin sheath, which is formed by Schwann cells in the peripheral nervous system and oligodendrocytes in the central nervous system. Axons containing such a covering are "myelinated." Neurons include sensory (afferent) neurons, which transmit impulses from receptors in the periphery to the brain and spinal cord and from lower to higher centers of the central nervous system. A neuron can also be motor (efferent) neurons which convey impulses from the brain and spinal cord to effectors in the periphery and from higher to lower centers of the central nervous system. Other neurons are association (connecting or interneuron) neurons which carry impulses from sensory neurons to motor neurons and are located within the central nervous system. The processes of afferent and efferent neurons arranged into bundles are called "nerves" when located outside the CNS or fiber tracts if inside the CNS.

"Neural tissue" includes any tissue that comprises a neural cell or a nerve. Other cells that may be present include one or more of oligodendrocytes, astrocytes, ependymal cells, microglial cells or Schwann cells.

The terms "astrocytes" and "astroglial cells" refer to a type of glial cell that become reactive and up-regulates intermediate filament (IF) proteins, such as glial fibrillary acid protein (GFAP) and vimentin (Vim), under pathological conditions or after transplantation in the brain and retina.

"GFAP" refers to "glial fibrillary acid protein" which is one of the major intermediate filament proteins of mature astrocytes. It is used as a marker to distinguish astrocytes from other glial cells during development.

As used herein, the phrase "axonal growth" or "axon growth" refers to the elongation or extension of an axon of a neural cell. An axon can elongate for distances of microns to meters. Extension or elongation of an axon is also referred to as "regeneration" of the axon of a neural cell and may result in the reestablishment of nerve cell connectivity.

As used herein, "spinal cord injury" means an injury in which the axons or nerve fibers of the spinal cord are interrupted, generally by mechanical forces.

As used herein, the term "scar" or "scarring" refers to a residual left by the healing of injured tissue. The residual can be manifested by a visible mark, by color, by palpable thickness, or by lack of compliance, or plasticity, or functional deficit. As used herein, the term "improved scar" or "improved scarring" or "reduced scarring" means that an injured tissue which has been treated with an agent capable of altering scar formation develops a residual that is less visible, or less thick, or more pliable and elastic, or possesses meaningful function, and is more like normal tissue than injured tissue that has not been treated by the agent.

As used herein, the term "spinal cord scarring" refers to the recruitment and proliferation of glial cells to the site of spinal cord injury. The densely packed cells (primarily reactive astrocytes) and their secretions form a dense cellular plaque known as the glial scar. This scar prevents axons from projecting through thus interfering with axonal regeneration and functional recovery.

The terms "parenteral administration" and "administered parenterally" are art-recognized and refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articulare, subcapsular, subarachnoid, intraspinal, epidural, intracerebral and intrasternal injection or infusion.

"Treatment," "treat," or "treating," as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition, i.e., arresting its development; (c) relieving and or ameliorating the disease or condition, i.e., causing regression of the disease or condition; or (d) curing the disease or condition, i.e., stopping its development or progression. The population of subjects treated by the methods of the invention includes subjects suffering from the undesirable condition or disease, as well as subjects at risk for development of the condition or disease.

As used herein, a "wound" is any disruption, from whatever cause, of normal anatomy (internal and/or external anatomy) including but not limited to traumatic injuries such as mechanical (i.e. contusion, penetrating), thermal, chemical, electrical, concussive and incisional injuries; elective injuries such as operative surgery and resultant incisional hernias, fistulas, etc.; acute wounds, chronic wounds, infected wounds, and sterile wounds, as well as wounds associated with disease states (i.e. ulcers caused by diabetic neuropathy or ulcers of the gastrointestinal or genitourinary tract). A wound is dynamic and the process of healing is a continuum requiring a series of integrated and interrelated cellular processes that begin at the time of wounding and proceed beyond initial wound closure through arrival at a stable scar. These cellular processes are mediated or modulated by humoral substances including but not limited to cytokines, lymphokines, growth factors, and hormones. In accordance with the subject invention, "wound healing" refers to improving, by some form of intervention, the natural cellular processes and humoral substances of tissue repair such that healing is faster, and/or the resulting healed area has less scaring and/or the wounded area possesses tissue strength that is closer to that of uninjured tissue and/or the wounded tissue attains some degree of functional recovery.

DETAILED DESCRIPTION

In accordance with the present invention there may be employed conventional molecular biology, microbiology, and recombinant DNA techniques within the skill of the art. Such techniques are explained fully in the literature. See, e.g., Sambrook et al, 2001, "Molecular Cloning: A Laboratory Manual"; Ausubel, ed., 1994, "Current Protocols in Molecular Biology" Volumes I-III; Celis, ed., 1994, "Cell Biology: A Laboratory Handbook" Volumes I-III; Coligan, ed., 1994, "Current Protocols in Immunology" Volumes I-III; Gait ed., 1984, "Oligonucleotide Synthesis"; Hames & Higgins eds., 1985, "Nucleic Acid Hybridization"; Hames & Higgins, eds., 1984, "Transcription And Translation"; Freshney, ed., 1986, "Animal Cell Culture"; IRL Press, 1986, "Immobilized Cells And Enzymes"; Perbal, 1984, "A Practical Guide To Molecular Cloning."

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

Therapeutic Uses

Spinal Cord Injury—Common causes of spinal cord injury include fractures of the vertebrae, which can damage the spinal cord from the concussive effect of injury due to displaced bony fragments, or damaged blood vessels, or contusion of emerging nerve roots. Dislocation of vertebrae can also cause spinal cord damage; dislocation is often the result of the rupture of an intervertebral disk, and may result in partial or complete severance of the spinal cord. Penetrating wounds can also cause severance or partial severance of the cord. Epidural hemorrhage and spinal subdural hematoma can result in progressive paraparesis due to pressure on the spinal cord. Examples of indirect injury to the spinal cord include damage induced by a blow to the head or a fall on the feet.

Intramedullary injury can be the result of direct pressure on the cord or the passage of a pressure wave through the cord, laceration of the cord by bone, or the rupture of a blood vessel during the passage of a pressure wave through the cord with a hemorrhage into the cord. Intramedullary bleeding and hematoma formation can also be caused by rupture of a weakened blood vessel. Ischemic damage can occur following compression of the anterior spinal artery, pressure on the anastomotic arteries, or damage to major vessels (Gilroy, in Basic Neurology, McGraw-Hill, Inc. New York, N.Y. (1990).

Spinal cord injuries can be divided into two categories, complete injuries and incomplete injuries. It is possible that the classification of the injury may change during recovery. Complete spinal cord injuries are usually characterized by the loss of sensation and motor ability and are generally associated with spinal cord injury caused by bruising, loss of blood to the spinal cord, or pressure on the spinal cord. Cut and severed spinal cords are rare. Generally, complete spinal cord injuries result in total loss of sensation and movement below the site of the injury.

Incomplete spinal cord injuries generally do not result in complete loss of movement and sensation below the injury site. A variety of patterns exist to classify such injuries including 1) anterior cord syndrome which results from damage to the motor and sensory pathways in the anterior areas of the spinal cord. Effects include loss of movement and overall sensation, although some sensations that travel by way of the still intact pathways can be felt; 2) central cord syndrome which results from injury to the center of the cervical area of the spinal cord. The damage affects the corticospinal tract, which is responsible for carrying signals between the brain and spinal cord to control movement. Patients suffering from central cord syndrome experience weakness or paralysis in the arms and some loss of sensory reception. The loss of strength and sensation is much less in the legs than in the arms. Many patients with central cord syndrome spontaneously recover motor function, and others experience considerable recovery in the first six weeks following the injury; 3) Brown-Sequard syndrome results from injury to the right or left side of the spinal cord. On the side of the body where the injury occurred, movement and sensation are lost below the level of the injury. On the side opposite the injury, temperature and pain sensation are lost due to the crossing of these pathways in the spinal cord; 4) injuries to individual nerve cells results in loss of sensory and motor function in the area of the body to which the injured nerve root corresponds. Thus, symptoms from these injuries vary depending on the location and function of the particular nerve root affected; 5) spinal contusions which are the most common type of spinal cord injury. The spinal cord is bruised, not severed, but the consequence is inflammation and bleeding from blood vessels near the injury. A spinal contusion may result in temporary (usually one to two days) incomplete or complete debilitation of the spinal cord or the incomplete or complete debilitation of the spinal cord may be longer term, including a permanent incomplete or complete debilitation of the spinal cord.

A goal of treating spinal cord injury includes promoting motor recovery. Another goal is promoting sensory recovery. Various modalities have been attempted to achieve such motor and sensory recovery, most with only limited success. These studies include application of various growth factors and cytokines to the site of injury as well as transplantation of brain-derived stem cells or healthy spinal cord tissue. Stem cell transplantation therapies are among the most promising therapies currently being studied (see, for example, Cummings, B. J., et al., Neurol Res 2006 28(5):474-81; Pallini, R., et al., Neurosurgery 2005 57(5):1014-25; Cummings, B. J., et al., PNAS USA 2005 102(39):14069-74; Sankar, V. et al., Neuroscience 2003 118(1):11-7).

It is an object of the present invention to use the compositions and methods described herein to promote spinal cord injury repair and functional recovery. Such methods utilize novel compositions, including but not limited to extraembryonic cytokine secreting cells (herein referred to as ECS cells), conditioned media and cell products derived therefrom, each alone and/or in combination with each other and/or with other agents including active and/or inactive agents. In a particular preferred embodiment, the methods utilize novel compositions including, but not limited to, amnion-derived multipotent progenitor cells (herein referred to as AMP cells), conditioned media derived therefrom (herein referred to as amnion-derived cellular cytokine solution or ACCS), and cell products derived therefrom, each alone and/or in combination with each other and/or with other agents including active and/or inactive agents. In a certain preferred embodiment, the AMP cells are pooled AMP cells and the ACCS is pooled ACCS.

The instant invention is based upon the discovery that ECS cells, conditioned medium therefrom, cell lysates therefrom, extracellular matrices therefrom, alone or in combination, as well as compositions of AMP cells can promote such spinal cord injury repair and functional recovery. Thus, using therapeutically effective amounts of ECS cells, including AMP cells, and/or conditioned medium and/or cell lysates from such cells, alone or in combination with each other and/or other agents, it is believed that all types of spinal cord injury will repair and heal and regain functionality more rapidly than similar spinal cord injuries left to heal naturally or which are treated with currently available methods. Other agents may include, but are not limited to, immature endogenous cells such as progenitor or stem cells recruited to the site of injury for reparative purposes by the therapeutically effective amounts of ECS cells, including AMP cells, and/or conditioned medium and/or cell lysates from such cells, alone or in combination with each other and/or other agents. It is also contemplated by the methods of the invention that the compositions described herein will prevent or reduce swelling and/or inflammation of the injured spinal cord.

In a preferred embodiment of the present invention, ECS cells, including AMP cells and/or conditioned medium therefrom (i.e. ACCS), and/or cell lysates thereof are administered to the injury to promote spinal cord injury healing and functional recovery in the patient. This direct administration can be as a single dose or repeated doses given at multiple designated intervals. It will be readily appreciated by those skilled in the art that the preferred dosage regimen will vary with the type and severity of the injury being treated. In addition, the direct administration to the injury may be directly to the spinal cord, the spinal roots and/or the spinal nerves, or any combination thereof.

Obtaining and Culturing of Cells

ECS cells—Various methods for isolating cells from the extraembryonic tissue, which may then be used to produce the ECS cells of the instant invention are described in the art (see, for example, US2003/0235563, US2004/0161419, US2005/0124003, U.S. Provisional Application Nos. 60/666, 949, 60/699,257, 60/742,067, 60/813,759, U.S. application Ser. No. 11/333,849, U.S. application Ser. No. 11/392,892, PCT/US06/011392, US2006/0078993, PCT/US00/40052, U.S. Pat. No. 7,045,148, US2004/0048372, and US2003/0032179).

Identifying ECS cells—Once extraembryonic tissue is isolated, it is necessary to identify which cells in the tissue have the characteristics associated with ECS cells (see definition above). For example, cells are assayed for their ability to secrete a unique combination of physiologically relevant cytokines at physiologically relevant levels into the extracellular space or into surrounding culture media. One particular non-limiting example of such suitable cells are those in which the cytokine or cytokines occurs in the physiological range of ~5.0-16 ng/ml for VEGF, ~3.5-4.5 ng/ml for Angiogenin, ~100-165 pg/ml for PDGF, ~2.5-2.7 ng/ml for TGFβ2, ~0.68 µg ml for TIMP-1 and ~1.04 µg/ml for TIMP-2. Skilled artisans will recognize that other suitable ECS cell populations are also obtainable using the methods described herein.

AMP cells—In a particular embodiment, AMP cell compositions are prepared using the steps of a) recovery of the amnion from the placenta, b) dissociation of the cells from the amniotic membrane, c) selecting then culturing of the cells in a basal medium with the addition of a naturally derived or recombinantly produced human protein; and optionally d) further proliferation of the cells using additional additives and/or growth factors. Details are contained in US Publication No. 2006-0222634-A1, which is incorporated herein by reference.

AMP cells are cultured as follows: The AMP cells are cultured in a basal medium. Such medium includes, but is not limited to, Epilife (Cascade Biologicals), Opti-pro, VP-SFM, IMDM, Advanced DMEM, K/0 DMEM, 293 SFM II (all made by Gibco; Invitrogen), HPGM, Pro 2935-CDM, Pro 293A-CDM, UltraMDCK, UltraCulture (all made by Cambrex), Stemline I and Stemline II (both made by Sigma-Aldrich), DMEM, DMEM/F-12, Ham's F12, M199, and other comparable basal media. Such media should either contain human protein or be supplemented with human protein. As used herein a "human protein" is one that is produced naturally or one that is produced using recombinant technology. "Human protein" also is meant to include a human fluid or derivative or preparation thereof, such as human serum or amniotic fluid, which contains human protein. Details on this procedure are contained in US Publication No. 2006-0222634-A1, which is incorporated herein by reference.

In a most preferred embodiment, the cells are cultured using a system that is free of animal products to avoid xeno-contamination. In this embodiment, the culture medium is Stemline I or II, Opti-pro, or DMEM, with human albumin added up to concentrations of 10%. The invention further contemplates the use of any of the above basal media wherein animal-derived proteins are replaced with recombinant human proteins and animal-derived serum, such as BSA, is replaced with human albumin. In preferred embodiments, the media is serum-free in addition to being animal-free. Details on this procedure are contained in US Publication No. 2006-0222634-A1, which is incorporated herein by reference.

In alternative embodiments, where the use of non-human serum is not precluded, such as for in vitro uses, the culture medium may be supplemented with serum derived from mammals other than humans, in ranges of up to 40%.

Additional proliferation—Optionally, other proliferation factors are used. In one embodiment, epidermal growth factor (EGF), at a concentration of between 0-1 µg/ml is used. In a preferred embodiment, the EGF concentration is around 10 ng/ml. Alternative growth factors which may be used include, but are not limited to, TGFα or TGFβ (5 ng/ml; range 0.1-100 ng/ml), activin A, cholera toxin (preferably at a level of about 0.1 µg/ml; range 0-10 µg/ml), transferrin (5 µg/ml; range 0.1-100 µg/ml), fibroblast growth factors (bFGF 40 ng/ml (range 0-200 ng/ml), aFGF, FGF-4, FGF-8; (all in range 0-200 ng/ml), bone morphogenic proteins (i.e. BMP-4) or other growth factors known to enhance cell proliferation.

Generation of Conditioned Medium

ECS conditioned medium—is obtained as described below for ACCS, except that ECS cells are used.

Generation of ACCS—The AMP cells of the invention can be used to generate ACCS. In one embodiment, the AMP cells are isolated as described herein and $1 \times 10^6$/mL cells are seeded into T75 flasks containing between 5-30 ml culture medium, preferably between 10-25 ml culture medium, and most preferably about 10 ml culture medium. The cells are cultured until confluent, the medium is changed and in one embodiment the ACCS is collected 1 day post-confluence. In another embodiment the medium is changed and ACCS is collected 2 days post-confluence. In another embodiment the medium is changed and ACCS is collected 4 days post-confluence. In another embodiment the medium is changed and ACCS is collected 5 days post-confluence. In a preferred embodiment the medium is changed and ACCS is collected 3 days post-confluence. In another preferred embodiment the medium is changed and ACCS is collected 3, 4, 5, 6 or more days post-confluence. In another particular embodiment the ACCS is collected on multiple days post confluence (i.e. on day 12 and day 15). Pooled ACCS is created by combining individual ACCS collections (i.e. combining day 12 and day 15 ACCS collections). Skilled artisans will recognize that other embodiments for collecting ACCS from AMP cell cultures, such as using other tissue culture vessels, including but not limited to cell factories, flasks, hollow fibers, or suspension culture apparatus, or collecting ACCS from sub-confluent and/or actively proliferating cultures, are also contemplated by the methods of the invention. It is also contemplated by the instant invention that the ACCS be cryopreserved following collection. It is also contemplated by the invention that ACCS be lyophilized following collection. Skilled artisans are familiar with cryopreservation and lyophilization methodologies.

The compositions of the invention can be prepared in a variety of ways depending on the intended use of the compositions. For example, a composition useful in practicing the invention may be a liquid comprising an agent of the invention, i.e. ECS cells, including AMP cells and/or ACCS, in solution, in suspension, or both (solution/suspension). The term "solution/suspension" refers to a liquid composition where a first portion of the active agent is present in solution and a second portion of the active agent is present in particulate form, in suspension in a liquid matrix. A liquid composition also includes a gel. The liquid composition may be aqueous or in the form of an ointment, salve, cream, or the like.

An aqueous suspension or solution/suspension useful for practicing the methods of the invention may contain one or more polymers as suspending agents. Useful polymers include water-soluble polymers such as cellulosic polymers and water-insoluble polymers such as cross-linked carboxyl-containing polymers. An aqueous suspension or solution/suspension of the present invention is preferably viscous or muco-adhesive, or even more preferably, both viscous and muco-adhesive.

Pharmaceutical Compositions

The present invention provides pharmaceutical compositions of ECS cells, including AMP cells and/or ACCS and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the composition is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, calcium sulfate derivatives and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Examples of suitable pharmaceutical carriers are described in "Remington's Pharmaceutical Sciences" by E. W. Martin, and still others are familiar to skilled artisans.

The pharmaceutical compositions of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Treatment Kits

The invention also provides for an article of manufacture comprising packaging material and a pharmaceutical composition of the invention contained within the packaging material, wherein the pharmaceutical composition comprises compositions of ECS cells, including AMP cells and/or ACCS. The packaging material comprises a label or package insert which indicates that the ECS cells, including AMP cells and/or ACCS can be used for treating spinal cord injury.

Formulation, Dosage and Administration

Compositions comprising ECS cells, including AMP cells and/or ACCS may be administered to a subject to provide various cellular or tissue functions, for example, to treat spinal cord injury due to trauma, surgery, etc. As used herein "subject" may mean either a human or non-human animal.

Such compositions may be formulated in any conventional manner using one or more physiologically acceptable carriers optionally comprising excipients and auxiliaries. Proper formulation is dependent upon the route of administration chosen. The compositions may be packaged with written instructions for their use in treating spinal cord injury. The compositions may also be administered to the recipient in one or more physiologically acceptable carriers. Carriers for the ECS cells, including AMP cells, may include but are not limited to solutions of phosphate buffered saline (PBS) or lactated Ringer's solution containing a mixture of salts in physiologic concentrations.

One of skill in the art may readily determine the appropriate concentration, or dose, of the ECS cells, including AMP cells and/or ACCS, for a particular purpose. The skilled artisan will recognize that a preferred dose is one which produces a therapeutic effect, such as functional recovery following spinal cord injury, in a patient in need thereof. Of course, proper doses of the ECS cells, including AMP cells and/or ACCS will require empirical determination at time of use based on several variables including but not limited to the severity and type of injury, disorder or condition being treated; patient age, weight, sex, health; other medications and treatments being administered to the patient; and the like. One of skill in the art will also recognize that number of doses (dosing regimen) to be administered needs also to be empirically determined based on, for example, severity and type of injury, disorder or condition being treated. In a preferred embodiment, one dose is sufficient. Other preferred embodiments contemplate 2, 3, 4, or more doses.

The present invention provides a method of treating a spinal cord injury by administering to a subject ECS cells, including AMP cells and/or ACCS in a therapeutically effective amount. By "therapeutically effective amount" is meant the dose of ECS cells, including AMP cells and/or ACCS that is sufficient to elicit a therapeutic effect. Thus, the concentration of ECS cells, including AMP cells and/or ACCS in an administered dose unit in accordance with the present invention is effective in the treatment spinal cord injury.

In further embodiments of the present invention, at least one additional agent may be combined with the ECS cells, including AMP cells and/or ACCS to enhance healing and functional recovery following spinal cord injury. Such agents include but are not limited to neuroregenerative agents, neuroprotective agents, neurotrophic factors, growth factors, cytokines, chemokines, antibodies, inhibitors, antibiotics, immunosuppressive agents, steroids, anti-fungals, anti-virals or other cell types. In particular, the neuroprotective agents is for example a dopamine D3 receptor agonist, the neurotrophic factors are BDNF, NT-3, NT-4, CNTF, NGF, or GDNF; the antibodies are for example IN-1 anti-NOGO antibodies; the inhibitor is for example the PDE4 inhibitor rollipr021; the immunosuppressive agents are for example corticosteroids (i.e. glucocorticoids), cyclosporine, tacrolimus, sirolimus, methotrexate, azathiopine, mercatopurine, cytotoxic antibiotics, polyclonal and monoclonal antibodies such as anti-T-cell receptor (CD23) and anti-IL2 receptor (CD25) antibodies, interferon, opioids, TNF binding proteins, mycophenolate, and small biological agents such as FTY720; the antibiotics are for example pikromycin, narbomycin, methymycin, neomethymycin; the steroid is for example methylprednisolone; and the other cell types are for example differentiated AMP cells, or a mixture of differentiated and undifferentiated AMP cells, or a mixture of AMP cells (differentiated and/or undifferentiated) and other cells such as neural stem cells or any other progenitor cell or cells that are treated in such a way as to augment the AMP cells or AMP cell activity. Inactive agents include carriers, diluents, stabilizers, gelling agents, delivery vehicles, ECMs (natural and synthetic), scaffolds, and the like. When the ECS cells, including AMP cells and/or ACCS are administered conjointly with other pharmaceutically active agents, even less of the ECS cells, including AMP cells and/or ACCS may be needed to be therapeutically effective.

ECS cells, including AMP cells and/or ACCS, can be administered by injection into a target site of a subject, preferably via a delivery device, such as a tube, e.g., catheter. In a preferred embodiment, the tube additionally contains a needle, e.g., a syringe, through which the cells (i.e. ECS cells, including AMP cells) and/or conditioned media (i.e. ACCS) can be introduced into the subject at a desired location. Specific, non-limiting examples of administering cells to subjects may also include administration by subcutaneous injection, intramuscular injection, intravenous injection, intraarterial injection, intracardiac injection, intradermal injection, intrathecal injection, epidural injection, intraperitoneal injection, intracerebral injection, direct injection into spinal cord tissue, or any injection that results in introduction into CNS tissues or spaces. Infusions are also contemplated by the methods of the invention (i.e. subdural, intrathecal or intracerebral infusion, or direct infusion into spinal cord tissue, or any injection that results in introduction into CNS tissues or spaces). If administration is intravenous, an injectable liquid suspension of cells can be prepared and administered by a continuous drip or as a bolus. In some instances, it may be appropriate to administer the ECS cells, including AMP cells and/or ACCS, using an infusion pump.

The timing of administration of ECS cells, including AMP cells and/or ACCS will depend upon the type and severity of the spinal cord injury being treated. In one embodiment, the ECS cells, including AMP cells and/or ACCS, are administered as soon as possible after the injury. In another embodiment, the ECS cells, including AMP cells and/or ACCS are administered more than one time following injury. In certain embodiments, the ECS cells, including AMP cells and/or ACCS, are administered at the time of stabilizing surgery. In still other embodiments, the ECS cells, including AMP cells and/or ACCS, are administered at the time of stabilizing surgery as well as after surgery. Such post-surgical administration may take the form of a single administration or multiple administrations.

Skilled artisans will recognize that any and all of the standard methods and modalities for treating spinal cord injury currently in clinical practice and clinical development are suitable for practicing the methods of the invention. Routes of administration, formulation, co-administration with other agents (if appropriate) and the like are discussed in detail elsewhere herein.

The administration of ECS cells, including AMP cells and/or ACCS may be in combination with other treatment modalities, for example, therapeutic cooling following spinal cord injury (see, for example, Guest J D, Dietrich W D (2005) Spinal cord ischemia and trauma. In: Therapeutic Hypothermia (Tisherman S A, Sterz F, eds), pp 101-118, Kluwver Academic Publishers; Casas C E, Herrera L P, Prusmack C, Ruenes G, Marcillo A, Guest J D (2005) Effects of epidural hypothermic saline infusion on locomotor outcome and tissue preservation after moderate thoracic spinal cord contusion in rats, J Neurosurg Spine 2:308-318; Bethea J R, Dietrich W D (2002) Targeting the host inflammatory response in traumatic spinal cord injury, Curr Opin Neurol 15:355-360; Yu C G, Jimenez O, Marcillo A E, Weider B, Bangerter K, Dietrich W D, Castro S, Yezierski R P (2000) Beneficial effects of modest systemic hypothermia on locomotor function and histopathological damage following contusion-induced spinal cord injury in rats. J Neurosurg 93:85-93) each of which is incorporated herein by reference.

ECS cells, including AMP cells, may also be inserted into a delivery device, e.g., a syringe, in different forms. For example, the cells can be suspended in a solution contained in such a delivery device. As used herein, the term "solution" includes a pharmaceutically acceptable carrier or diluent in which the cells of the invention remain viable. Pharmaceutically acceptable carriers and diluents include saline, aqueous buffer solutions, solvents and/or dispersion media. The use of such carriers and diluents is well known in the art. The solution is preferably sterile and fluid to the extent that easy syringability exists. Preferably, the solution is stable under the conditions of manufacture and storage and preserved against the contaminating action of microorganisms such as bacteria and fungi through the use of, for example, parabens, chlorobutanol, phenol, ascorbic acid, thimerosal, and the like. Solutions of the invention can be prepared by incorporating ECS cells, including AMP cells or partially or fully differentiated cells as described herein, in a pharmaceutically acceptable carrier or diluent and, as required, other ingredients enumerated above.

ECS cells, including AMP cells, may be administered systemically (for example intravenously) or locally (for example by direct application under visualization during surgery). For such administration, the cells may be in an injectable liquid suspension preparation or in a biocompatible medium which is injectable in liquid form and becomes semi-solid at the site of damaged tissue. A controllable endoscopic delivery device can be used so long as the needle lumen or bore is of sufficient diameter (e.g. 30 gauge or larger) that shear forces will not damage the cells being delivered.

Cells may be administered in a manner that permits them to graft to the intended tissue site and reconstitute or regenerate the functionally deficient area. ECS cells, including AMP cells, can be used in therapy by direct administration, or as part of a bioassist device that provides temporary or permanent organ function. In this respect, ECS cells, including AMP cells, may be grown in a bioreactor to provide extracorporeal organ support for organ relief, such as in the case of a liver assist device, to provide a plentiful source of cells for transplantation to restore organ function, or provide a source of conditioned medium that may be used to stimulate tissue regeneration and/or healing.

Alternatively, ECS cells, including AMP cells, may be transplanted into the recipient where the cells will proliferate and differentiate to form new cells and tissues thereby providing the physiological processes normally provided by that tissue, or may produce factors that cause the migration and/or differentiation of cells in the area of the transplant. Tissues are an aggregation of similarly specialized cells united in the performance of a particular function. Tissue is intended to encompass all types of biological tissue including both hard and soft tissue. Also included in the definition of tissues are neural tissues, including the functional cells of the nervous system, neurons, and various supporting cells such as glial cells, oligodendrocytes, and the like.

Support matrices into which the ECS cells, including AMP cells, can be incorporated or embedded include matrices which are recipient-compatible and which degrade into products which are not harmful to the recipient. These matrices provide support and protection for ECS cells, including AMP cells, in vivo and are, therefore, the preferred form in which such cells are transplanted into the recipient subjects.

Natural and/or synthetic biodegradable matrices are examples of such matrices. Natural biodegradable matrices include plasma clots, e.g., derived from a mammal, collagen, fibronectin, and laminin matrices. Suitable synthetic material for a cell transplantation matrix must be biocompatible to preclude migration and immunological complications, and should be able to support extensive cell growth and differentiated cell function. It must also be resorbable, allowing for a completely natural tissue replacement. The matrix should be configurable into a variety of shapes and should have sufficient strength to prevent collapse upon implantation. Recent studies indicate that the biodegradable polyester polymers made of polyglycolic acid fulfill all of these criteria (Vacanti, et al. J. Ped. Surg. 23:3-9 (1988); Cima, et al. Biotechnol. Bioeng. 38:145 (1991); Vacanti, et al. Plast. Reconstr. Surg. 88:753-9 (1991)). Other synthetic biodegradable support matrices include synthetic polymers such as polyanhydrides, polyorthoesters, and polylactic acid. Further examples of synthetic polymers and methods of incorporating or embedding cells into these matrices are also known in the art. See e.g., U.S. Pat. Nos. 4,298,002 and 5,308,701. Other suitable matrices are bioerodable matrices. An example of such a matrix is one made with alginate and alginate lyase (see, for example, Ashton, R. S., et al., Biomaterials, December 2007, Vol 28, Issue 36, pp. 5518-5525).

Attachment of the cells to the polymer may be enhanced by coating the polymers with compounds such as basement membrane components, agar, agarose, gelatin, gum arabic, collagens types I, II, III, IV and V, fibronectin, laminin, glycosaminoglycans, mixtures thereof, and other materials known to those skilled in the art of cell culture. All polymers for use in the matrix must meet the mechanical and biochemical parameters necessary to provide adequate support for the cells with subsequent growth and proliferation. The polymers can be characterized with respect to mechanical properties such as tensile strength using an Instron tester, for polymer molecular weight by gel permeation chromatography (GPC), glass transition temperature by differential scanning calorimetry (DSC) and bond structure by infrared (IR) spectroscopy, with respect to toxicology by initial screening tests involving Ames assays and in vitro teratogenicity assays, and implantation studies in animals for immunogenicity, inflammation, release and degradation studies.

One of the advantages of a biodegradable polymeric matrix is that angiogenic and other bioactive compounds (i.e. neurotrophic factors) can be incorporated directly into the support matrix so that they are slowly released as the support matrix degrades in vivo. As the cell-polymer structure is vascularized and the structure degrades, ECS cells, including AMP cells, may differentiate according to their inherent characteristics. Factors, including nutrients, growth factors, inducers of differentiation or de-differentiation (i.e., causing differentiated cells to lose characteristics of differentiation and acquire characteristics such as proliferation and more general function), products of secretion, immunomodulators, inhibitors of inflammation, regression factors, biologically active compounds which enhance or allow ingrowth of the lymphatic network or nerve fibers, hyaluronic acid, and drugs, which are known to those skilled in the art and commercially available with instructions as to what constitutes an effective amount, from suppliers such as Collaborative Research, Sigma Chemical Co., vascular growth factors such as vascular endothelial growth factor (VEGF), epidermal growth factor (EGF), and heparin binding epidermal growth factor like growth factor (HB-EGF), could be incorporated into the matrix or be provided in conjunction with the matrix. Similarly, polymers containing peptides such as the attachment peptide RGD (Arg-Gly-Asp) can be synthesized for use in forming matrices (see e.g. U.S. Pat. Nos. 4,988,621, 4,792, 525, 5,965,997, 4,879,237 and 4,789,734).

In another example, the ECS cells, including AMP cells, may be transplanted in a gel matrix (such as Gelfoam from Upjohn Company) which polymerizes to form a substrate in which the cells can grow. A variety of encapsulation technologies have been developed (e.g. Lacy et al., Science 254:1782-84 (1991); Sullivan et al., Science 252:718-712 (1991); WO 91/10470; WO 91/10425; U.S. Pat. No. 5,837,234; U.S. Pat. No. 5,011,472; U.S. Pat. No. 4,892,538). During open surgical procedures involving direct physical access to the damaged spinal cord tissue, all of the described forms of ECS cell, including AMP cell, delivery preparations are available options. These cells can be repeatedly transplanted at intervals until a desired therapeutic effect, i.e. functional recovery from spinal cord injury, is achieved.

The present invention also relates to the use of ECS cells, including AMP cells, in three dimensional cell and tissue culture systems to form structures analogous to tissue counterparts in vivo. The resulting tissue will survive for prolonged periods of time, and perform tissue-specific functions following transplantation into the recipient host. Methods for producing such structures are described in U.S. Pat. Nos. 5,624,840 and 6,428,802, which are incorporated herein in their entireties.

The three-dimensional matrices to be used are structural matrices that provide a scaffold for the cells, to guide the process of tissue formation. Scaffolds can take forms ranging from fibers, gels, fabrics, sponge-like sheets, and complex 3-D structures with pores and channels fabricated using complex Solid Free Form Fabrication (SFFF) approaches. Cells cultured on a three-dimensional matrix will grow in multiple layers to develop organotypic structures occurring in three dimensions such as ducts, plates, and spaces between plates that resemble sinusoidal areas, thereby forming new liver tissue. Thus, in preferred aspects, the present invention provides a scaffold, multi-layer cell and tissue culture system. As used herein, the term "scaffold" means a three-dimensional (3D) structure (substrate and/or matrix) that cells grow in or on. It may be composed of biological components, synthetic components or a combination of both. Further, it may be naturally constructed by cells or artificially constructed. In addition, the scaffold may contain components that have biological activity under appropriate conditions. The structure of the scaffold can include a mesh, a sponge or can be formed from a hydrogel.

Examples of such scaffolds include a three-dimensional stromal tissue or living stromal matrix which has been inoculated with stromal cells that are grown on a three dimensional support. The extracellular matrix proteins elaborated by the stromal cells are deposited onto the scaffold, thus forming a living stromal tissue. The living stromal tissue can support the growth of ECS cells, including AMP cells, or partially or fully differentiated cells derived therefrom later inoculated to form the three-dimensional cell culture. Examples of other three dimensional scaffolds are described in U.S. Pat. No. 6,372, 494.

The design and construction of the scaffolding to form a three-dimensional matrix is of primary importance. The matrix should be a pliable, non-toxic, injectable porous template for vascular ingrowth. The pores should allow tissue ingrowth such as vascular and/or neural ingrowth. These are generally interconnected pores in the range of between approximately 100 and 300 microns, i.e., having an interstitial spacing between 100 and 300 microns, although larger openings can be used. The matrix should be shaped to maximize surface area, to allow adequate diffusion of nutrients, gases and growth factors to the cells on the interior of the matrix and to allow the ingrowth of new blood vessels and connective tissue. At the present time, a porous structure that is relatively resistant to compression is preferred, although it has been demonstrated that even if one or two of the typically six sides of the matrix are compressed, that the matrix is still effective to yield tissue growth.

The polymeric matrix may be made flexible or rigid, depending on the desired final form, structure and function. For repair of a defect, for example, a flexible fibrous mat is cut to approximate the entire defect then fitted to the surgically prepared defect as necessary during implantation. An advantage of using the fibrous matrices is the ease in reshaping and rearranging the structures at the time of implantation.

A sponge-like structure can also be used to create a three-dimensional framework. The structure should be an open cell sponge, one containing voids interconnected with the surface of the structure, to allow adequate surfaces of attachment for sufficient ECS cells, including AMP cells, or differentiated cells to form a viable, functional implant.

The invention also provides for the delivery of ECS cells, including AMP cells, including compositions described herein, in conjunction with any of the above support matrices as well as amnion-derived membranes. Such membranes may be obtained as a by-product of the process described herein for the recovery of AMP cells, or by other methods, such as are described, for example, in U.S. Pat. No. 6,326,019 which describes a method for making, storing and using a surgical graft from human amniotic membrane, US 2003/0235580 which describes reconstituted and recombinant amniotic membranes for sustained delivery of therapeutic molecules, proteins or metabolites, to a site in a host, U.S. 2004/0181240, which describes an amniotic membrane covering for a tissue surface which may prevent adhesions, exclude bacteria or inhibit bacterial activity, or to promote healing or growth of tissue, and U.S. Pat. No. 4,361,552, which pertains to the preparation of cross-linked amnion membranes and their use in methods for treating burns and wounds. In accordance with the present invention, ECS cells, including AMP cells, may be grown on such membranes, added to the membrane in either an undifferentiated, partially differentiated or fully differentiated form, or ECS cell, including AMP cell, conditioned media (i.e. ACCS) or cell lysates may be added to such membranes. Alternatively, amniotic tissue in which amnion epithelial cells have not been stripped away may be used to deliver ECS cells, including AMP cells, to a particular site. In all cases, ECS cells, including AMP cells, used in conjunction with amniotic tissue or other matrices can be used in combination with other therapeutically useful cells and/or cells expressing biologically active therapeutics such as those described in below.

ECS cells, including AMP cells, may be genetically engineered to produce a particular therapeutic protein. Therapeutic protein includes a wide range of biologically active proteins including, but not limited to, growth factors, neurotrophic factors, enzymes, hormones, cytokines, inhibitors of cytokines, blood clotting factors, peptide growth and differentiation factors. Particular differentiated cells may be engineered with a protein that is normally expressed by the particular cell type. For example, neural cells can be engineered to produce chemical transmitters or neurotrophic factors or axonal guidance factors.

Methods which are well known to those skilled in the art can be used to construct expression vectors containing a nucleic acid encoding the protein of interest linked to appropriate transcriptional/translational control signals. See, for example, the techniques described in Sambrook et al, 2001, "Molecular Cloning: A Laboratory Manual"; Ausubel, ed., 1994, "Current Protocols in Molecular Biology" Volumes I-III; Celis, ed., 1994.

Suitable methods for transferring vector or plasmids into ECS cells, including AMP cells, or cells differentiated therefrom include lipid/DNA complexes, such as those described in U.S. Pat. Nos. 5,578,475; 5,627,175; 5,705,308; 5,744,335; 5,976,567; 6,020,202; and 6,051,429. Suitable reagents include lipofectamine, a 3:1 (w/w) liposome formulation of the poly-cationic lipid 2,3-dioleyloxy-N-[2(sperminecarboxamido)ethyl]-N,N-d-imethyl-1-propanaminium trifluoroacetate (DOSPA) (Chemical Abstracts Registry name: N-[2-(2, 5-bis[(3-aminopropyl)amino]-1-oxpentyl)amino)ethyl-]-N, N-dimethyl-2,3-bis(9-octadecenyloxy)-1-propanamin-trifluoroacetate), and the neutral lipid dioleoyl phosphatidylethanolamine (DOPE) in membrane filtered water. Exemplary is the formulation Lipofectamine 2000™ (available from Gibco/Life Technologies #11668019). Other reagents include: FuGENE™ 6 Transfection Reagent (a blend of lipids in non-liposomal form and other compounds in 80% ethanol, obtainable from Roche Diagnostics Corp. #1814443); and LipoTAXI™ transfection reagent (a lipid formulation from Invitrogen Corp., #204110). Transfection of ECS cells can be performed by electroporation, e.g., as described in Roach and McNeish (Methods in Mol. Biol. 185:1 (2002)). Suitable viral vector systems for producing stem cells with stable genetic alterations may be based on adenoviruses, lentiviruses, retroviruses and other viruses, and may be prepared using commercially available virus components.

ECS cells, including AMP cells, or cells that are partially differentiated or fully differentiated therefrom may be administered or transplanted to a subject to provide various cellular or tissue functions specific to the differentiated cell type. For example, in certain embodiments, the present invention provides for administration of neural cells derived from ECS cells, including AMP cells, for treatment of spinal cord injury and scarring.

The ECS cells, including AMP cells, may be used in in vitro priming procedures that result in neural stem cells becoming neurons when grafted into non-neurogenic or neurogenic areas of the CNS. For details and examples, see US2003/0235563 and US2004/0161419, both which are incorporated herein by reference.

Methods of Differentiating ECS cells, including AMP cells, and Differentiated Cell Types The ECS cells may be contacted with various growth factors (termed differentiation factors) that influence differentiation of such stem cells into particular cell types such as neural cells, hepatocytes, pancreatic cells, vascular endothelial cells, muscle cells and cardiomyocytes. For examples, see US2003/0235563 and US2004/0161419, the contents of which are incorporated herein by reference.

The literature is replete with additional differentiation protocols for embryonic as well as non-embryonic stem or other multipotent cells, including stem cells. One skilled in the art will recognize that any of these protocols can be applied to the ECS cell, including AMP cell, compositions described herein to produce partially or fully differentiated cells for such uses. Exemplary protocols are set forth below:

Ectoderm (neural differentiation). Clusters are removed from the large-scale apparatus and transferred to ultra-low adherence 6-well plates. The differentiation protocol described by Carpenter, M. K. et al. (2001) Exp Neurol 172: 383-397 for human embryonic stem cells is followed for differentiation as follows. 10 mM all-trans retinoic acid (RA) will added to the culture medium (80% KO-DMEM, 1 mM glutamine, 0.1 mM β-mercaptoethanol, 1% non-essential amino acids, and 20% FBS) containing these clusters in suspension. After 4 days in suspension, clusters are plated onto poly-L-lysine/fibronectin-coated plates in differentiation medium (DMEM/F-12 with B27 (Gibco), 10 ng/ml human epidermal growth factor (hEGF), 10 ng/ml human basic fibroblast growth factor (hbFGF) (Gibco), 1 ng/ml human platelet-derived growth factor-AA (hPDGF-AA) (R & D Systems), and 1 ng/ml human insulin-like growth factor-1 (hIGF-1) (R & D Systems) for 3 days. After 3 days under these conditions, the cells are harvested for RNA or fixed. Fixed cells are immunostained for nestin, polysialylated neural cell adhesion molecule (PS-NCAM), and A2B5. RNA is analyzed by reverse transcriptase-PCR (RT-PCR) for nestin, GFAP and MAP-2.

Differentiated cells derived from ECS cells may be detected and/or enriched by the detection of tissue-specific markers by immunological techniques, such as flow immunocytochemistry for cell-surface markers, immunohistochemistry (for example, of fixed cells or tissue sections) for intracellular or cell-surface markers, Western blot analysis of cellular extracts, and enzyme-linked immunoassay, for cellular extracts or products secreted into the medium. The expression of tissue-specific gene products can also be detected at the mRNA level by Northern blot analysis, dot-blot hybridization analysis, or by reverse transcriptase initiated polymerase chain reaction (RT-PCR) using sequence-specific primers in standard amplification methods.

Alternatively, differentiated cells may be detected using selection markers. For example, ECS cells can be stably transfected with a marker that is under the control of a tissue-specific regulatory region as an example, such that during differentiation, the marker is selectively expressed in the specific cells, thereby allowing selection of the specific cells relative to the cells that do not express the marker. The marker can be, e.g., a cell surface protein or other detectable marker, or a marker that can make cells resistant to conditions in which they die in the absence of the marker, such as an antibiotic resistance gene (see e.g., in U.S. Pat. No. 6,015,671).

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees centigrade, and pressure is at or near atmospheric.

Example 1

Preparation of AMP Cell Compositions

Recovery of AMP cells—AMP cells were dissociated from starting amniotic membrane using the dissociation agents PXXIII, and trypsin. The average weight range of an amnion was 18-27 g. The number of cells recovered per g of amnion was about $10\text{-}15\times10^6$ for dissociation with PXXIII and $5\text{-}8\times 10^6$ for dissociation with trypsin.

Method of obtaining selected AMP cells: Cells were plated immediately upon isolation from the amnion. After ~2 days in culture non-adherent cells were removed and the adherent cells were kept. This attachment to plastic tissue culture vessel is the selection method used to obtain the desired population of cells. Adherent and non-adherent AMP cells appear to have a similar cell surface marker expression profile but the adherent cells have greater viability and are the desired population of cells. Adherent AMP cells were cultured until they reached ~120,000-150,000 cells/cm$^2$. At this point, the cultures were confluent. Suitable cell cultures will reach this number of cells between ~5-14 days. Attaining this criterion is an indicator of the proliferative potential of the AMP cells and cells that do not achieve this criterion are not selected for further analysis and use. Once the AMP cells reach ~120,000-150,000 cells/cm$^2$, they were collected and cryopreserved. This collection time point is called p0 and all subsequent analyses are done with thawed p0 AMP cells.

Example 2

Generation of ACCS

The AMP cells of the invention can be used to generate ACCS. The AMP cells were isolated as described herein and $10\times10^6$/mL cells were seeded into T75 flasks containing 10 ml culture medium. The cells are cultured until confluent, the medium is changed and ACCS was collected 3 days post-confluence. Skilled artisans will recognize that other embodiments for collecting ACCS from confluent cultures, such as using other tissue culture vessels, including but not limited to cell factories, flasks, hollow fibers, or suspension culture apparatus, are also contemplated by the methods of the invention. It is also contemplated by the instant invention that the ACCS be cryopreserved following collection.

Example 3

Use of AMP Cells to Treat Spinal Cord Injury in NOD SCID Mice

Transplantation of AMP cells—Nine days after contusion injury (see, for example, Constantini, S., and Young, W. (1994), J. Neurosurg. 80, 97-111; Anderson, A. J., et al., Journal of Neurotrauma 21 (12), 1831-1846 for animal models), AMP cells were transplanted and vehicle was injected (controls) into two different sites, the injury epicenter or the adjacent nervous tissue parenchyma.

Analysis—Open field locomotor testing is the standard of the spinal cord injury field, because it is the only task which allows the investigator to evaluate a full spectrum of potential recovery, from complete paralysis (a 0 on the BBB or BMS) to fully normal locomotion (a 21 on the BBB, and a 9 on the BMS). However, these are nonlinear (ordinal) scales. It is not a direct comparison of the number of points of change that is relevant, but rather what these points represent in terms of specifically recovered locomotor function. In these tasks, animals move freely in a circular area for a four minutes testing period while two investigators blinded to experimental group observe and rank the animals based on specific criteria on each testing scale. In the case of the range of recovery for the animals in this pilot, the key criterion scored by the investigators involves the ability to achieve consistent stepping and complete coordinated "passes". Each unbroken series of movements across the arena greater than three body lengths is defined as a pass. Normal animals make one hindlimb step for each forelimb step; missed steps decrease the score an animal achieves on the scale.

Results—The results suggest an improvement in spinal cord epicenter AMP cell-transplanted animals versus control animals, which is significant at some time points and exhibits a trend at others. The improvement observed for the epicenter transplanted animals reflects the gain of coordinated locomotion. Using this limited experimental design, it was not possible to determine whether transplantation into the adjacent parenchyma could result in improved locomotor activity. In addition, histological analyses need to be done to determine if there is evidence of differentiation and/or regeneration.

Example 4

Histology of Spinal Cord From AMP Cell Transplanted NOD SCID Mice

Perfusion and Tissue Collection. Mice are anesthetized and transcardially perfused with 30 ml of PBS followed by 100 ml of 4% paraformaldehyde. Spinal cords are dissected, and the segments corresponding to T2-T5, T6-T12, and T13-L3 are blocked. Blocks are post-fixed overnight in 4% paraformaldehyde. For immunocytochemistry, blocks are equilibrated in 30% sucrose/PBS for 12 h, embedded in OCT compound, and frozen at −65° C. in isopentane for sectioning. Tissue sections are analyzed for markers indicating differentiation and/or regeneration of cells.

Example 5

Acute (2 Day Delay) AMP Cell Transplantation after SCI May Improve Functional Locomotor Recovery Based on the behavioral data from the 9 day delay experiment (Example 3 above), it appears that there may be a wound healing effect in the animals receiving epicenter AMP cell transplantation. It is predicted that an effect on wound healing may be enhanced at earlier timepoints after SCI, when there is greater opportunity to modify secondary injury processes. Accordingly, it may be optimal to investigate the effect of a more acute transplantation time on locomotor outcome. A 2 day delay has been selected based on the clinical relevance of surgical intervention within the first 48 hours post-SCI. The comparative data between 2 and 9 day post-SCI transplants provides insight into the most appropriate focus in terms of timing and predicted outcome.

The experimental groups are as follows: Group 1-2 days post-injury, epicenter, AMP cells; Group 2-2 days post-injury, epicenter, vehicle; Group 3-2 days post-injury, rostral-caudal, AMP cells; Group 4-2 days post-injury, rostral-caudal, vehicle. All procedures are performed under isoflurane anesthesia. Animals are anesthetized, the spinal cord exposed at T9 and a moderate contusion injury (50 kd) is produced using the IH Impactor. 2 days post-SCI, human AMP cells are injected via a pulled glass micropipette attached to a nanoinjector either into four sites around the injury center (2 rostral and 2 caudal, right and left of the center) or as a single injection directly into the injury epicenter. 250 nl of cells is injected for each rostral caudal site for a total of 1 µl for each animal. 2 µl of cells is injected for the epicenter site. Parenchymal injections in this case provide a valuable cellular control and are an essential group for analysis. Cells are injected at a concentration of 75,000 cells per µl sterile HBSS. Vehicle consists of sterile HBSS. After suturing, all animals are monitored until they recover from anesthetic, and maintained on water jacketed heating pads at 37° C. overnight. Animals are housed in group cages with Alpha-dri bedding and monitored a minimum of 2×/day for a minimum of 3 weeks post-SCI for signs of debilitation or skin lesions, and their bladders expressed a minimum of 2×/day by manual crede during this period. Animals are monitored 1×/day thereafter until sacrifice.

The principal endpoints are behavioral analysis of the groups and quantitative determination of lesion volume and tissue sparing using MRI. Supplemental analysis of locomotor recovery includes terminal assessment of horizontal ladderbeam (Cummings et al., 2007) and/or CatWalk (Noldus Inc.) performance, based on selection of the task most appropriate to the range of recovery of function observed in control and transplanted animals. Supplemental unbiased stereological assessment of the histology of AMP cell engraftment and survival, as well as astroglial scarring, proteoglycan deposition, and regeneration of descending serotonergic tracts is also conducted as described previously (Engesser-Cesar et al., 2007). Animals are tested on BMS (2 days pre-SCI, 2 days post-SCI, 1 week post-SCI, and each week for 4 weeks), gait analysis (pre-SCI and 1 day prior to sacrifice), and ladderbeam (pre-SCI and 1 day prior to sacrifice). Animals are euthanized 4 weeks post-SCI. At this time, animals are perfused and the spinal cords dissected by vertebral root level, and prepared for ex vivo MRI analysis of lesion volume, as described previously (Nishi et al., 2007).

Example 6

AMP Cells May Evidence Immunoprivileged when Transplanted into Non-Immunosuppressed, Non-Immunodeficient Mice AMP cells may have an immunoprivileged status after transplantation, even in a xenograft paradigm. This experiment is designed to test the rejection of AMP cells when transplanted into C57BL/6 mice that have received a moderate contusion injury as described above, but no immunosuppressive treatment. The optimal transplant locus (epicenter versus parenchyma) and time (2 d versus 9 d delay post-SCI) is selected based on the previous experiments, and mice are maintained as described under Example 5.

Mice are sacrificed at 1 week (n=5), 2 weeks (n=5) or 4 weeks (n=5) post-transplantation for histological analysis of surviving AMP cells. The principal endpoint for this study is histological, focusing on quantification of engrafted cells and the immune rejection response, although open-field locomotor recovery data is collected. Dissected spinal cords are sectioned parasagittally on a sliding microtome at 30 µm, and sections stained using human specific nuclear antigen (Chemicon), ED1 (Serotec) to visualize the macrophages/microglia response, anti-neutrophil antibody (Serotec) to visualize the neutrophil response, and CD8 (Serotec) to visualize the T-cell response. Engraftment of viable AMP cells is quantified by unbiased stereological analysis of stained sections sampled in a ⅙ series.

Example 7

Is ACCS Sufficient to Promote Recovery of Function after SCI, or Synergistic when Administered in Combination with AMP Cells?

There is evidence to suggest that the synthesis of a combination of trophic or other factors by AMP cells may in and of itself provide a number of wound healing effects. This experiment tests whether this effect is sufficient to promote recovery after SCI when administered alone, or whether it may act synergistically with transplanted AMP cells to further promote recovery of function after SCI.

The optimal transplant locus (epicenter versus parenchyma) and time (2 day versus 9 day delay post-SCI) is selected based on the previous experiments, and mice are injured, transplanted, and maintained as described under Example 5. Groups are as follows: Group 1—optimal time epicenter, ACCS; Group 2—optimal time, epicenter, AMP cells; Group 3—optimal time, epicenter, ACCS+AMP cells; Group 4—optimal time, epicenter, vehicle.

The principal endpoints of this study are behavioral analysis of the groups and quantitative determination of lesion volume and tissue sparing using MRI as described under Experiment 5. Supplemental unbiased stereological assessment of the histology of human cell engraftment and survival, as well as astroglial scarring, proteoglycan deposition, and regeneration of descending serotonergic tracts is also conducted as described under Experiment 5.

The present invention may be embodied in other specific forms without departing from the spirit or essential attributes thereof. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Throughout the specification various publications have been referred to. It is intended that each publication be incorporated by reference in its entirety into this specification.

What is claimed is:

1. A method for stimulating growth or regeneration of spinal cord cells following spinal cord injury in a patient in need thereof comprising administering to the patient a therapeutically effective amount of a composition comprising Amnion-derived Multipotent Progenitor (AMP) cells cultured from CD117 negative and CD90 negative freshly isolated AMP cells, wherein the spinal cord cells are selected from the group consisting of neurons, oligodendrocytes, astrocytes, microglial cells, and ependymal cells.

2. The method of claim 1 wherein the AMP cells are administered in combination with other agents and/or treatment modalities, wherein the other agents are selected from the group consisting of neuroregenerative agents, neuroprotective agents, neurotrophic factors, growth factors, cytokines, chemokines, antibodies, inhibitors, antibiotics, immunosuppressive agents, steroids, anti-fungals, anti-virals or other cell types, and the other treatment modality is therapeutic cooling, wherein the neuroprotective agent is dopamine D3 receptor agonists, the neurotrophic factors are selected from the group consisting of BDNF, NT-3, NT-4, CNTF, NGF, or GDNF; the antibodies are IN-1 anti-NOGO antibodies; the inhibitor is the PDE4 inhibitor rollipram; the immunosuppressive agents are selected from the group consisting of corticosteroids, cyclosporine, tacrolimus, sirolimus, methotrexate, azathiopine, mercatopurine, cytotoxic antibiotics, anti-T-cell receptor (CD23) and anti-IL2 receptor (CD25) antibodies, interferon, opioids, TNF binding proteins, mycophenolate, and FTY720; the antibiotics are selected from the group consisting of pikromycin, narbomycin, methymycin and neomethymycin; the steroid is methylprednisolone; and the other cell types are selected from the group consisting of differentiated amnion-derived multipotent progenitor cells, a mixture of differentiated and undifferentiated AMP cells, and a mixture of AMP cells and/or cells differentiated from AMP cells and neural stem cells.

3. A method for ameliorating scarring following spinal cord injury in a patient in need thereof comprising administering to the patient a therapeutically effective amount of a composition comprising AMP cells cultured from CD117 negative and CD90 negative freshly isolated AMP cells.

4. The method of claim 3 wherein the AMP cells are administered in combination with other agents and/or treatment modalities, wherein the other agents are selected from the group consisting of neuroregenerative agents, neuroprotective agents, neurotrophic factors, growth factors, cytokines, chemokines, antibodies, inhibitors, antibiotics, immunosuppressive agents, steroids, anti-fungals, anti-virals or other cell types, and the other treatment modality is therapeutic cooling wherein the neuroprotective agent is dopamine D3 receptor agonists, the neurotrophic factors are selected from the group consisting of BDNF, NT-3, NT-4, CNTF, NGF, or GDNF; the antibodies are IN-1 anti-NOGO antibodies; the inhibitor is the PDE4 inhibitor rollipram; the immunosuppressive agents are selected from the group consisting of corticosteroids, cyclosporine, tacrolimus, sirolimus, methotrexate, azathiopine, mercatopurine, cytotoxic antibiotics, anti-T-cell receptor (CD23) and anti-IL2 receptor (CD25) antibodies, interferon, opioids, TNF binding proteins, mycophenolate, and FTY720; the antibiotics are selected from the group consisting of pikromycin, narbomycin, methymycin and neomethymycin; the steroid is methylprednisolone; and the other cell types are selected from the group consisting of differentiated amnion-derived multipotent progenitor cells, a mixture of differentiated and undifferentiated AMP cells, and a mixture of AMP cells and/or cells differentiated from AMP cells and neural stem cells.

5. A method for neuroprotecting spinal cord neurons following spinal cord injury in a patient in need thereof comprising administering to the patient a therapeutically effective amount of a composition comprising AMP cells cultured from CD117 negative and CD90 negative freshly isolated AMP cells.

6. The method of claim 5 wherein the AMP cells are administered in combination with other agents and/or treatment modalities, wherein the other agents are selected from the group consisting of neuroregenerative agents, neuroprotective agents, neurotrophic factors, growth factors, cytokines, chemokines, antibodies, inhibitors, antibiotics, immunosuppressive agents, steroids, anti-fungals, anti-virals or other cell types, and the other treatment modality is therapeutic cooling wherein the neuroprotective agent is dopamine D3 receptor agonists, the neurotrophic factors are selected from the group consisting of BDNF, NT-3, NT-4, CNTF, NGF, or GDNF; the antibodies are IN-1 anti-NOGO antibodies; the inhibitor is the PDE4 inhibitor rollipram; the immunosuppressive agents are selected from the group consisting of corticosteroids, cyclosporine, tacrolimus, sirolimus, methotrexate, azathiopine, mercatopurine, cytotoxic antibiotics, anti-T-cell receptor (CD23) and anti-IL2 receptor (CD25) antibodies, interferon, opioids, TNF binding proteins, mycophenolate, and FTY720; the antibiotics are selected from the group consisting of pikromycin, narbomycin, methymycin and neomethymycin; the steroid is methylprednisolone; and the other cell types are selected from the group consisting of differentiated amnion-derived multipotent progenitor cells, a mixture of differentiated and undifferentiated AMP cells, and a mixture of AMP cells and/or cells differentiated from AMP cells and neural stem cells.

* * * * *